United States Patent
Voic

(10) Patent No.: US 9,636,187 B2
(45) Date of Patent: May 2, 2017

(54) ATOMIZED-FLUID SHIELD FOR SURGERY AND METHOD OF USE

(75) Inventor: Dan Voic, Cedar Grove, NJ (US)

(73) Assignee: MISONIX INCORPORATED, Farmingdale, NY (US)

( * ) Notice: Subject to any disclaimer, the term of this patent is extended or adjusted under 35 U.S.C. 154(b) by 129 days.

(21) Appl. No.: 11/986,424

(22) Filed: Nov. 21, 2007

(65) Prior Publication Data

US 2009/0126741 A1 May 21, 2009

(51) Int. Cl.
| | | |
|---|---|---|
| A61F 5/37 | (2006.01) |
| A61B 90/00 | (2016.01) |
| A61B 90/40 | (2016.01) |
| A61B 17/32 | (2006.01) |

(52) U.S. Cl.
CPC .............. A61B 90/05 (2016.02); A61B 90/40 (2016.02); *A61B 2017/320072* (2013.01)

(58) Field of Classification Search
CPC ......... A61B 19/38; A61B 19/42; A61B 19/10; A61B 19/08; A61B 19/081
USPC ....... 128/846, 849, 856, 917, 897, 898, 851, 128/850, 852, 853, 854, 855; 606/215; 600/119; 604/162, 163; 250/519.1, 250/515.1; 83/83
See application file for complete search history.

(56) References Cited

U.S. PATENT DOCUMENTS

| | | | | |
|---|---|---|---|---|
| 3,416,520 A | * | 12/1968 | Creager, Jr. ............ | A61B 19/08 128/850 |
| 4,188,945 A | * | 2/1980 | Wenander ...................... | 128/850 |
| 4,581,538 A | * | 4/1986 | Lenhart ....................... | 250/519.1 |
| 4,736,762 A | * | 4/1988 | Wayman ........................ | 52/2.14 |
| 4,887,615 A | * | 12/1989 | Taylor ........................... | 128/850 |
| 4,998,538 A | * | 3/1991 | Charowsky et al. ......... | 128/856 |
| 5,074,316 A | * | 12/1991 | Dowdy ......................... | 128/849 |
| 5,178,162 A | * | 1/1993 | Bose ............................. | 128/849 |
| 5,300,059 A | * | 4/1994 | Rubinstein et al. .......... | 604/408 |
| 5,316,541 A | * | 5/1994 | Fischer .......................... | 600/21 |
| 5,514,133 A | * | 5/1996 | Golub et al. .................. | 606/1 |
| 5,653,705 A | * | 8/1997 | de la Torre et al. ......... | 606/1 |
| 5,725,495 A | * | 3/1998 | Strukel et al. ................ | 604/44 |
| 5,848,992 A | * | 12/1998 | Hart et al. ............... | 604/103.03 |
| 6,402,724 B1 | | 6/2002 | Smith et al. | |
| 7,393,322 B2 | * | 7/2008 | Wenchell ....................... | 600/208 |
| 2003/0191371 A1 | * | 10/2003 | Smith et al. .................. | 600/210 |
| 2003/0204200 A1 | * | 10/2003 | Rufener ......................... | 606/172 |
| 2004/0211431 A1 | | 10/2004 | Musso et al. | |
| 2006/0124138 A1 | * | 6/2006 | Dusenbery et al. .......... | 128/849 |
| 2006/0293630 A1 | * | 12/2006 | Manna et al. ................ | 604/327 |

* cited by examiner

*Primary Examiner* — Victoria J Hicks
(74) *Attorney, Agent, or Firm* — R. Neil Sudol; Henry D. Coleman

(57) ABSTRACT

A surgical shield includes an at least partially rigid shield member extending in at least two spatial dimensions, at least one flexible sheet member, and a coupling element. The shield member has an aperture traversable by a surgical instrument, while the coupling element is provided on the shield member for releasably connecting the shield member to the instrument. The flexible sheet member is attached to the shield member so as to define, with the shield member, an enclosure having one open side opposing the shield member.

5 Claims, 4 Drawing Sheets

ATOMIZED-FLUID SHIELD FOR SURGERY AND METHOD OF USE

BACKGROUND OF THE INVENTION

This invention relates to a system of devices for shielding the operator from both atomized fluid and waste liquid generated during surgical procedures and associated methods of use.

Over the past 30 years, several ultrasonic tools have been invented which can be used to ablate or cut tissue in surgery. Such devices are disclosed by Wuchinich et al. in U.S. Pat. No. 4,223,676 and Idemoto et al. in U.S. Pat. No. 5,188,102.

In practice, these surgical devices include a blunt tip hollow probe that vibrates at frequencies between 20 kc and 100 kc, with amplitudes up to 300 microns or more. Such devices ablate tissue by either producing cavitation bubbles which implode and disrupt cells, tissue compression and relaxation stresses (sometimes called the jackhammer effect) or by other forces such as micro streaming of bubbles in the tissue matrix. The effect is that the tissue becomes liquefied and separated. It then becomes emulsified with an irrigant solution. The resulting emulsion is then aspirated from the site. Bulk excision of tissue is possible by applying the energy around and under an unwanted tissue mass such as a tumor to separate it from the surrounding structure. The surgeon can then lift the separated or excised tissue mass out using common tools such as forceps.

The probe or tube is excited by a transducer of either the piezoelectric or magnetostrictive type that transforms an alternating electrical signal within the frequencies indicated into a longitudinal or transverse vibration. When the probe is attached to the transducer, the two become a single element with series and parallel resonances. The designer will try to tailor the mechanical and electrical characteristics of these elements to provide the proper frequency of operation. Most of the time, the elements will have a long axis that is straight and has the tip truncated in a plane perpendicular to the long axis. This is done for simplicity and economic considerations. In almost all applications, whether medical or industrial, such an embodiment is practical and useful.

However, when the devices are used in open field surgery, particularly when the operative site is on the skin or slightly below, a side effect of the ultrasonic probe interaction with fluids becomes apparent. This is the ability of the ultrasonic vibrating tool to break up fluid and aerosol them such that the particles of fluid may be projected into the operating room atmosphere and either inhaled or otherwise contaminate people or surfaces.

The ability of ultrasonic probes to atomize fluid is well known. Many patents have been issued for just such hardware, such as U.S. Pat. No. 5,516,043, U.S. Pat. No. 4,153,201, U.S. Pat. No. 4,337,896, and U.S. Pat. No. 4,541,564, among many others. These devices have application in industry and medicine where it is desired to create fine particles of fluid and transport them to an airstream or onto a work surface. In operation, a fluid is introduced to the distal end of the vibrating probe. The frequency of vibration may be from 20 to 200 kHz or higher. The vibrating tip breaks the surface tension of the fluid and projects small amounts of fluid off the surface. The natural phenomenon of fluid to coalesce to a sphere in space creates small particles, which by their low mass and aerodynamic nature are easily suspended in air. Depending upon variables such as frequency of vibration, amplitude and liquid properties, ultrasonic atomizers can produce atomized particles with small diameters.

In the operating room, this atomization has caused concern since the fluids being atomized can contain blood, virus particles, bacteria or other objectionable constituents. This phenomenon of aerosoling contaminants is not limited to ultrasonic aspirators alone. Medical lasers can produce smoke when ablating tissue that contains viruses as well. It is well documented that the virus that causes vaginal warts may be present in laser smoke. When the smoke contacts operating room personnel, warts will appear on lips and other mucous membranes. Several inventions have been developed to combat this smoke problem. One such device is the smoke extractor unit. This is a vacuum pump, chemical filter and pickup hose assembly. In practice, the pickup funnel is placed near the operative sight. The air surrounding the site is sucked into the extractor funnel, similar to a vacuum cleaner effect. The smoke and objectionable elements are removed with the chemical filter. The air is then exhausted back into the room.

Although these devices work reasonably well with laser smoke, they do not provide solutions to all of the issues involved with ultrasonic surgery. The aerosols emitted by the ultrasonic probe are liquid in nature and will contaminate the chemical filter. The liquid will drip out of the filter, causing contamination that must be disinfected and cleansed. In addition, the air volume required for capture of the aerosols causes a draft or breeze around the wound, which could lead to contamination of the wound bed from other sources within the room.

Other devices have been proposed, such as in the U.S. Pat. No. 5,848,998 to Marasco, which discloses a closed bag placed around the limb with apertures for insertion of the ultrasound tool. The shield will trap the atomized fluids and contain the irrigant flow for collection later. In practice, these inventions have been shown to have some limitations. One problem is that the shield must be sized and shaped for the particular part of the body to be operated on. In addition, the apertures must be located over the wound. Since the shield is not totally elastic, it is often not possible to position the aperture in close proximity to the wound itself. Also, the shield becomes wet on the inside with atomized particles and becomes cloudy, which inhibits free vision of the operative site. In cases where suction is applied to the shield to aspirate the collected fluid, the shield will collapse on the limb, further impeding efficient treatment of the patient.

It is therefore desired to find a means to reduce the escape of aerosols into the general operating room atmosphere while not impeding the line of sight of the surgeon nor impeding convenient access to the wound.

OBJECTS OF THE INVENTION

An object of the present invention is to provide an improved ultrasonic surgical method for use ancillary to the debridement of wounds or ablation of tissue in open field procedures.

A more particular object of the present invention is to provide a means to localize the droplets generated by ultrasonic surgical aspirators when used to debride wounds or ablate tissue in open field procedures.

Another relatively specific object of the present invention is to provide a means to prevent the atomized particles from blowing back into the operators breathing zone.

It is a further object of the present invention to provide such a means for atomized effluent suppression without restricting access to wound site or impeding the surgeon's line of sight.

These and other objects of the invention will be apparent from the drawings and descriptions herein. Although every object of the invention is attained in at least one embodiment of the invention, there is not necessarily any embodiment which attains all of the objects of the invention.

SUMMARY OF THE INVENTION

A surgical shield comprises, in accordance with the present invention, an at least semi-rigid shield support member extending in at least two spatial dimensions and at least one flexible sheet member. The shield support member has an aperture traversable by a surgical instrument. A separate coupling element is optionally provided on the shield support member for releasably connecting the shield support member to the instrument or to an appendage (typically the hand or arm) of a user. Alternatively, the material of the shield support member may be sufficiently resilient in the area of the aperture to releasably couple with the instrument or user appendage in a friction-lock engagement. The at least one flexible sheet member is attached to the shield support member so as to define, optionally with the shield support member, an enclosure having one open side opposing the aperture.

In one particular embodiment of the present invention, the sheet member is one of a plurality of flexible sheet members each attached to the shield support member and collectively with the shield member defining the enclosure. The sheet members form a lateral wall of the enclosure, while the shield support member forms an upper wall of the enclosure.

Pursuant to a feature of the particular embodiment, the shield support member has a perimetral edge and the sheet members are attached to the shield support member at the perimetral edge. The shield support member may be substantially planar and made of a substantially rigid or at least semi-rigid transparent material. The sheet members may similarly be formed of substantially flexible transparent material.

Pursuant to another feature of the particular embodiment, the sheet members overlap one another to thereby define at least one access path into the enclosure through the lateral wall. The access path is disposed between adjacent sheet members.

Preferably, the sheet members have a sufficient length, in a direction extending away from the shield support member, so that when ends of the sheet members opposite the shield support member are placed into contact with a patient and the instrument is operated with the shield support member and sheet members attached, the vast majority of the fluid droplets escaping a surgical site during operation of the instrument fail to reach the shield support member.

The sheet members and the shield support member may be provided along inner surfaces facing into the enclosure with a coating of a hydrophilic composition, thereby enhancing visibility of a surgical field surrounded by the sheet members.

The coupling member, if provided, may be adapted for attaching the shield support member to a handle of the instrument.

Where there is but a single sheet member, that sheet member may form a lateral wall of the enclosure, while the shield support member forms an upper wall of the enclosure. The sheet member may be provided with a slit or an aperture defining at least one access path into the enclosure through the lateral wall. The slit or aperture may be provided with a cover patch (forming a labyrinthine seal with the sheet member) that may be deformed to permit access through the slit or aperture. Preferably, the sheet member is attached to the shield support member at a perimetral edge thereof, the shield support member is substantially planar, the shield support member and the sheet member are made of transparent material, and the sheet member has a sufficient length, in a direction extending away from the shield support member, so that when an end of the sheet member opposite the shield support member is placed into contact with a patient and the instrument is operated with the shield support member and the at least one sheet member attached, fluid droplets escaping a surgical site during operation of the instrument substantially fail to reach the shield support member. Thus the field of view of the surgical site remains clear.

A surgical shield comprises, in accordance with a particular feature of the present invention and at least one panel member. The at least one panel defines one open side engageable about a periphery with a patient to form an enclosure. The at least one panel member includes at least one shield support member having an aperture traversable by a surgical instrument. A coupling element is optionally provided on the shield support member for releasably connecting the shield support member to the instrument or to an appendage (finger, hand or arm) of a user. Alternatively, the shield support member may be sufficiently resilient in the area of the aperture to form a friction coupling with the instrument or user appendage. The open side of the enclosure opposes the aperture. The at least one panel is provided along an inner surface facing into the enclosure with a coating of a hydrophilic composition, thereby enhancing visibility of a surgical field. The shield support member may likewise be provided along an inner surface facing into the enclosure with a coating of the hydrophilic composition.

Coating the inner surface of the shield with a hydrophilic substance reduces the surface tension of the atomized fluid. This has the effect of sheeting the liquid instead of allowing droplets to form. This improves the visualization of the operative sight and reduces operation time, since the surgeon does not have to stop to remove the drops before proceeding.

A surgical method in accordance with the present invention utilizes a surgical instrument and a shield, the shield comprising an at least semi-rigid shield support member extending in at least two spatial dimensions, the shield support member having an aperture and at least one flexible sheet member attached to the shield support member so as to define an enclosure having one open side opposing the aperture. The method comprises inserting at least a distal end portion of the instrument through the aperture in the shield member, releasably coupling the instrument or an appendage of the user to the shield support member, manipulating the shield so as to place the open side of the enclosure against a patient, thereafter operating the instrument to perform a surgical operation at a surgical site on the patient, and, during the operating of the instrument, maintaining the at least one sheet member in contact with the patient and the shield support member at such a distance from the patient that a vast majority of fluid droplets escaping the surgical site during operation of the instrument fail to reach the shield support member so that the surgical site remains effectively visible through the shield.

Where the sheet member forms a lateral wall of the enclosure, the shield support member forms an upper wall of the enclosure, and the sheet member defines at least one access path into the enclosure through the lateral wall, the method further comprises inserting a distal end portion of an ancillary surgical instrument along the access path while the at least one sheet member is in contact with the patient.

The coupling of the shield to the instrument may include attaching the shield support member to a handle of the instrument. The instrument may be an ultrasonic surgical device.

During the preparation of the patient for surgery, the shield is removed from its packaging. The shield may be sterile or unsterile, depending upon the type of surgery to be performed. The shield is placed over the ultrasonic probe and may be temporarily attached to the probe or transducer by a coupling element providing a friction fit or other means known to the art.

DEFINITIONS

The terms "substantially rigid" and "at least semi-rigid are used herein to denote a material that is able to retain its shape under its own weight. "Substantially rigid" or "at least semi-rigid" means that the material can be completely rigid but also encompasses polymeric or plastic materials that can bend when sufficient manual force is applied. Under moderately extreme forces, such materials will fold or fracture.

The term "substantially planar" is used herein to denote a three-dimensional body whose extent in two orthogonal dimensions is much greater than in a third orthogonal dimension. Under this definition, a flat panel that is warped or a shallow concave panel is substantially planar.

The phrase "fluid droplets substantially fail to reach a shield member" is used herein to describe a situation where vast majority of the fluid droplets escaping a surgical site during operation of the instrument fail to reach the shield member. Pursuant to the objects of the invention, the numbers of drops that reach the shield member are so few as to cause the user no difficulty in peering through the shield and observing a surgical site during an ultrasonic or other surgical procedure.

A "hydrophilic" coating is one that reduces the surface tension of atomized aqueous droplets that fall on the coating. A hydrophilic coating in the present invention has the effect of sheeting the liquid instead of allowing droplets to form during deposition of an atomized spray on the coating. This spreading of the liquid improves the visualization of the operative sight and reduces operation time, since the surgeon does not have to stop to remove the drops before proceeding.

DETAILED DESCRIPTION

Figure 1:
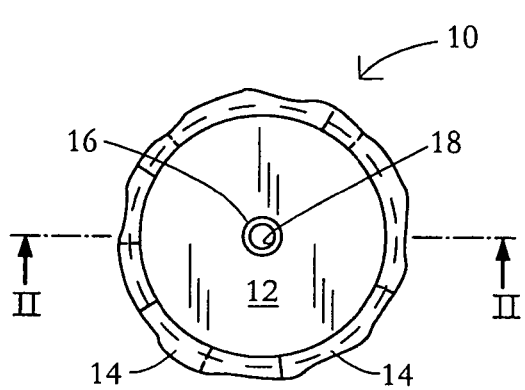
FIG. 1 is a schematic top plan view of a surgical shield in accordance with the present invention.
Figure 2:
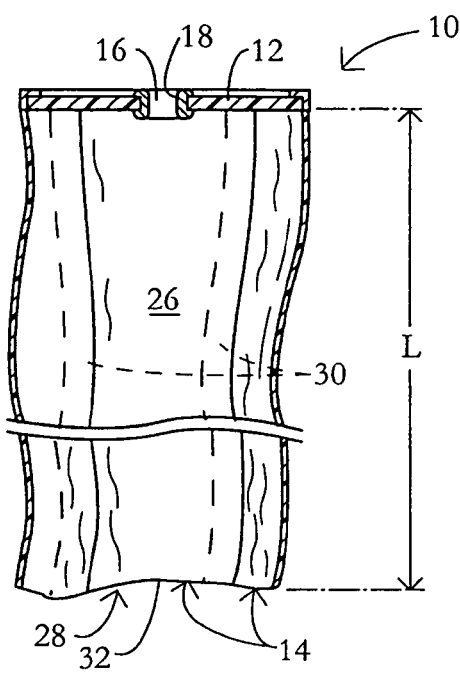
FIG. 2 is a schematic cross-sectional view of the surgical shield of FIG. 1, taken along line II-II.
Figure 3:
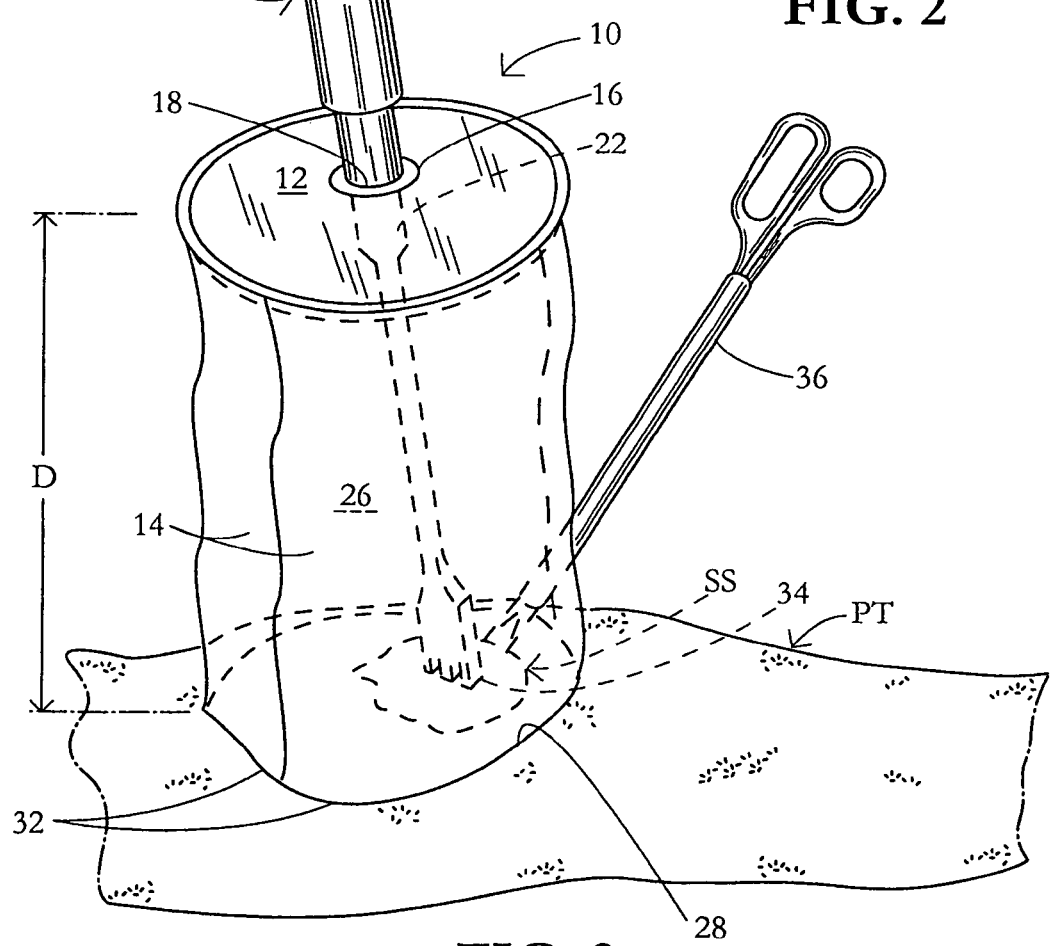
FIG. 3 is a schematic perspective view of the shield of FIGS. 1 and 2, showing use of the shield in an ultrasonic wound debriding procedure.

As shown in FIGS. 1-3, a surgical shield 10 comprises a shield support member 12, a plurality of flexible sheet members 14, and an annular resilient coupling element 16. Shield support member 12 is an at least semi-rigid sheet or web member particularly in the form of a circular, rectangular or other geometric shaped disk, that is, a flat or planar member, and has a central aperture 18 traversable by an ultrasonic surgical instrument 20. Coupling element 16 is exemplarily made at least in part of a polymeric foam or rubber material and is provided on shield support member 12 around aperture 18 for releasably connecting the shield support member to a shaft 22 or a handle 24 of instrument 20. Sheet members 14 are attached to shield member 10 so as to define therewith an enclosure 26 having one open side 28 opposing the shield member. Sheet members 14 form a lateral wall (not separately designated) of enclosure 26, while shield support member 12 forms an upper wall of the enclosure.

Shield support member 12 has a perimetral edge 28 and sheet members 14 are attached to the shield member at or along the perimetral edge. Shield support member 12 is made of a substantially rigid or at least semi-rigid transparent material, while sheet members 14 are formed of a substantially flexible transparent material.

Sheet members 14 overlap one another, forming an overlap zone 30, to thereby define multiple ancillary access paths into enclosure 26 through the lateral wall formed by the sheet members. The access paths are each disposed in an access zone corresponding to a respective overlap zone 30 between two adjacent sheet members 14 that overlap to form a labyrinthine seal.

In a surgical procedure that utilizes ultrasonic instrument 20 for cleaning tissue at a surgical site SS on patient PT (FIG. 3), a distal end portion of instrument 20 is inserted through aperture 18. Shield support member 12 is secured to instrument 20 by a friction fit owing to coupling element 16. Instrument 20 with shield 10 attached thereto is then moved over patient PT so that edges or ends 32 of sheet members 14 are in contact with the patient and surround surgical site SS. During the ultrasonic wound cleaning operation, instrument 20 is held by the surgeon so that an operative tip 34 is in contact with surgical site SS and so that shield support member 12 is disposed at a substantial distance D from the patient PT. In addition, instrument 20 together with shield 10 is so manipulated during the surgical procedure that the edges 32 of sheet members 14 are maintained in contact with the patient, thereby retaining the integrity of enclosure 26. One or more ancillary instruments 36 may be inserted along respective access paths between adjacent sheet members 14.

Sheet members 14 have a length L (FIG. 2), as measured in a direction extending away from shield support member 12. Typically sheet length L is greater than shield distance D, so that enclosure 26 is substantially closed. Length L is large enough so that when ends or edges 32 of the sheet members opposite the shield member are placed into contact with a patient PT and instrument 20 is operated with the shield member and sheet members attached (FIG. 3), the vast majority of the fluid droplets escaping a surgical site SS during operation of the instrument fail to reach the shield member. The droplets or atomized particles that reach shield support member 12 are too few to prevent effective visualization of surgical site SS through shield support member 12.

Figure 6:
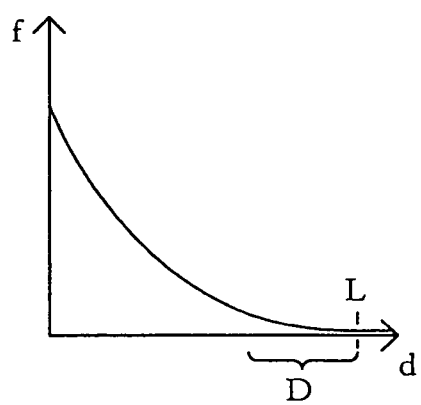
FIG. 6 is a graph showing an atomized particle distribution as a function of distance from a surgical site.

FIG. 6 diagrammatically depicts a distribution of atomized particles as a function of distance d from surgical site SS. Typically, distance D of shield support member 12 from surgical site SS is approximately equal to, but slightly less, than sheet length L. The proportion of the atomized particles reaching shield support member 12 to the total atomized particles generated during a surgical procedure is small, at the most.

Sheet members 14 and shield support member 12 may be provided along inner surfaces facing into enclosure 25 with a transparent coating of a hydrophilic composition, thereby enhancing visibility of a surgical field surrounded by the sheet members. Suitable hydrophilic polymers for this application include polyvinyl alcohol, polyvinyl pyrrolidone, and hydroxyethylmethacrylate (HEMA).

Figure 4:
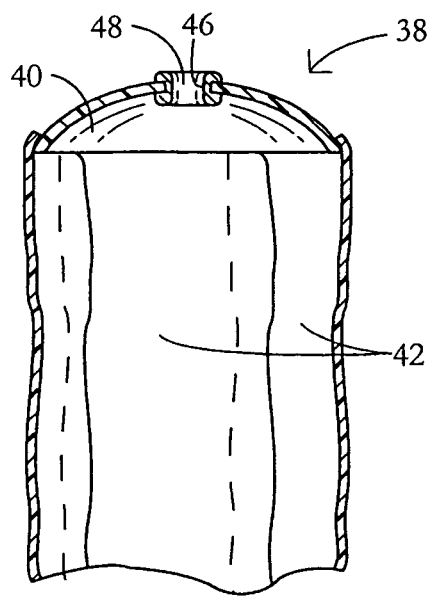
FIG. 4 is schematic cross-sectional view of another surgical shield in accordance with the present invention.

FIG. 4 shows another surgical shield 38 having a shield support member 40 in the form of a substantially rigid sheet or web member having a bowl shape and made of a transparent material and optionally provided along an inner surface with a hydrophilic coating. Multiple overlapping transparent and flexible sheet members 42 are attached to shield support member 40 about an edge or periphery thereof to form an enclosure 44. Shield support member 40 is provided with at least one aperture 46 and a resilient coupling element 48 inserted through the aperture and clamped to the shield member by internal spring forces enhancing a friction fit. Surgical shield 38 is used in the same manner as shield 10.

Figure 5:
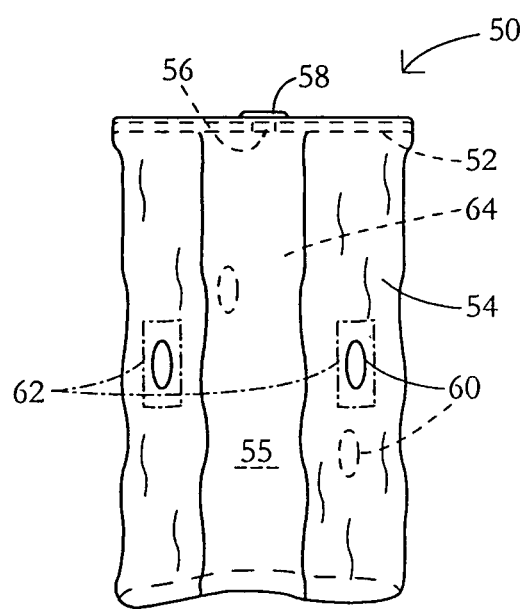
FIG. 5 is schematic cross-sectional view of a further surgical shield in accordance with the present invention.

As depicted in FIG. 5, a further surgical shield 50 includes a shield support member 52 in the form of a substantially rigid planar sheet or web member made of a transparent material and optionally provided along an inner surface with a hydrophilic coating. A single tubular sheet member 54 is attached to shield support member 52 about an edge or periphery thereof to form an enclosure 55. Sheet member 54 is made of transparent flexible material and may be provided along an inner surface with a hydrophilic coating. Shield member 50 is provided with at least one aperture 56 and a resilient coupling element 58 inserted through the aperture and clamped to the shield member by internal spring forces enhancing a friction fit. Sheet member 54 may be provided with a plurality of openings 60 (e.g., slits or holes) covered by flaps 62 of transparent flexible material. Flaps 62 may be lifted or pushed to the side to enable insertion of a distal end portion of at least one ancillary surgical instrument (e.g. instrument 36, FIG. 3) through one of the openings 60. Alternatively or additionally, ancillary instruments 36 may be provided access to enclosure 55 via a passage formed between overlapping end portions 64 of tubular sheet member 42. Sheet member 54 forms a lateral wall, while shield support member 52 forms an upper wall of enclosure 55. Surgical shield 50 is used in basically the same manner as shield 10.

Sheet members 42 of shield 38 and sheet member 54 of shield 50 have a length (not designated), as measured in a direction extending away from shield support members 40 and 52, that is sufficiently large so that when ends or edges of the sheet members 42 and 54 opposite the respective shield support member 40 and 52 are placed into contact with a patient PT and instrument 20 is operated with the shield member and sheet members attached (FIG. 3), the vast majority of the fluid droplets escaping a surgical site SS during operation of the instrument fail to reach the shield member. The droplets or atomized particles that reach shield support member 40 or 52 are too few to prevent effective visualization of surgical site SS through the shield member.

Figure 7:
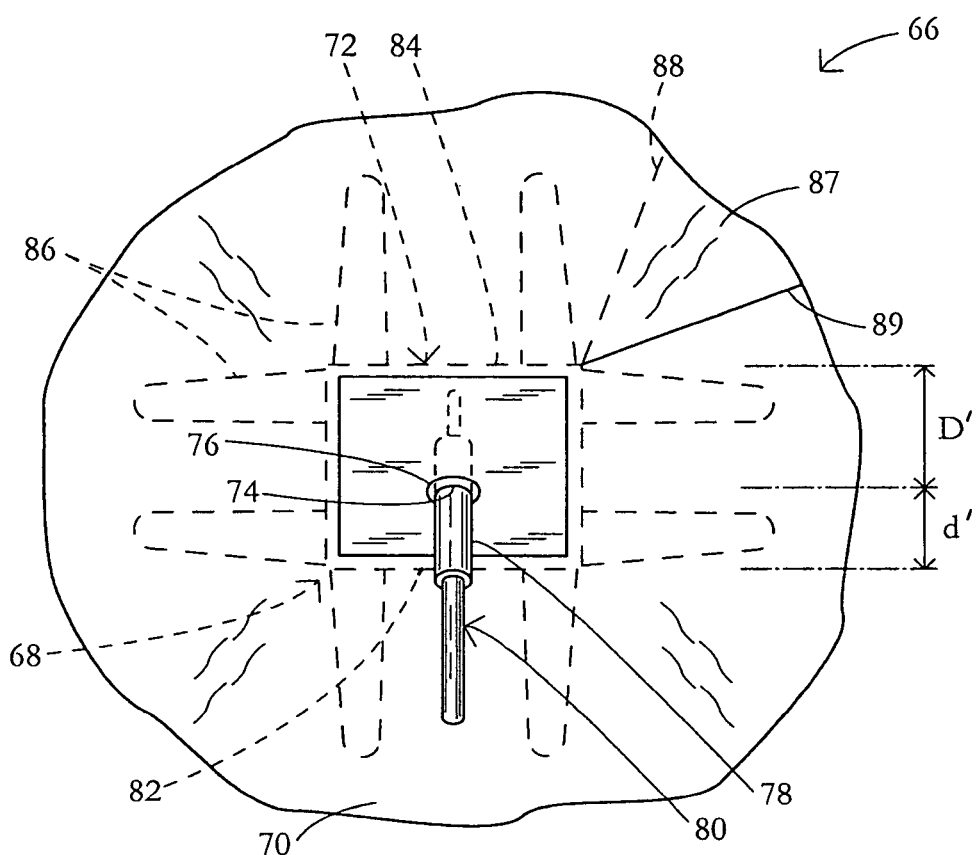
FIG. 7 is a schematic top view of an additional surgical shield in accordance with the present invention.

As depicted in FIG. 7 a surgical shield 66 includes a square or rectangular shield support member 68 and an elongate flexible sheet panel 70 attached to support member 68 along a perimetral edge 72 thereof to form a shield skirt. Shield support member 68 is made of a substantially rigid or at least semi-rigid transparent polymeric material, while sheet panel or skirt 70 is made of a flexible transparent polymeric material. Panel or skirt 70 is exemplarily attached to shield support member 68 by adhesive or by thermal or ultrasonic welding. Shield support member 68 is eccentrically formed with an aperture 74 provided with a coupling member 76 for forming a sealing engagement with a shaft 78 of an ultrasonic surgical instrument 80. Aperture 74 is spaced a distance d' from one linear edge 82 of shield support member 68 and a distance D' from an opposite linear edge 84 of the shield support member, distance D' being sufficiently larger than distance d' to facilitate visualization of a surgical site through that portion of the shield support member between aperture 74 and forward linear edge 84. Shield support member 68 includes a plurality of outwardly extending fingers or ribs 86 that hold sheet or skirt 70 outwardly in the manner and away from the surgical site. Fingers or ribs 86 may be integrally formed parts of shield support member 68 or may be separately formed and attached to the main body of the shield support member by adhesive or thermal or ultrasonic welding. Sheet of skirt 70 includes an area 87 overlap bounded on opposite sides by leading and trailing edges 88 and 89 of the sheet or skirt.

Figure 8:
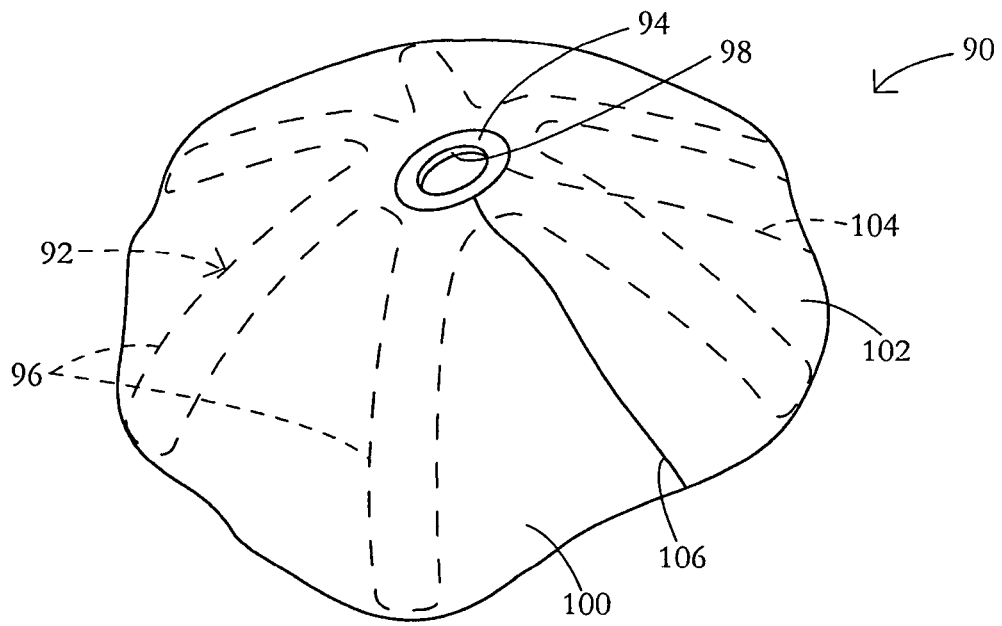
FIG. 8 is a schematic perspective view of yet another surgical shield in accordance with the present invention.

As illustrated in FIG. 8, another surgical shield 90 comprises a shield support member 92 made of substantially rigid or at least semi-rigid sheet or web material and having a central body or hub 94 and a plurality of arcuate spokes, fingers or ribs 96 extending outwardly and downwardly away from hub 94. Central body or hub 94 is provided with an aperture 98 having a coupling capability for sealingly engaging a shaft of an ultrasonic instrument (not shown). A flexible sheet 100 is attached, e.g., adhesively bonded or thermally or ultrasonically welded, to central body or hub 94 and spokes, fingers or ribs 96 to form an umbrella-like surgical shield 90. An area 102 is a region of overlapping opposite ends 104 and 106 of sheet or skirt 70.

Figure 9:
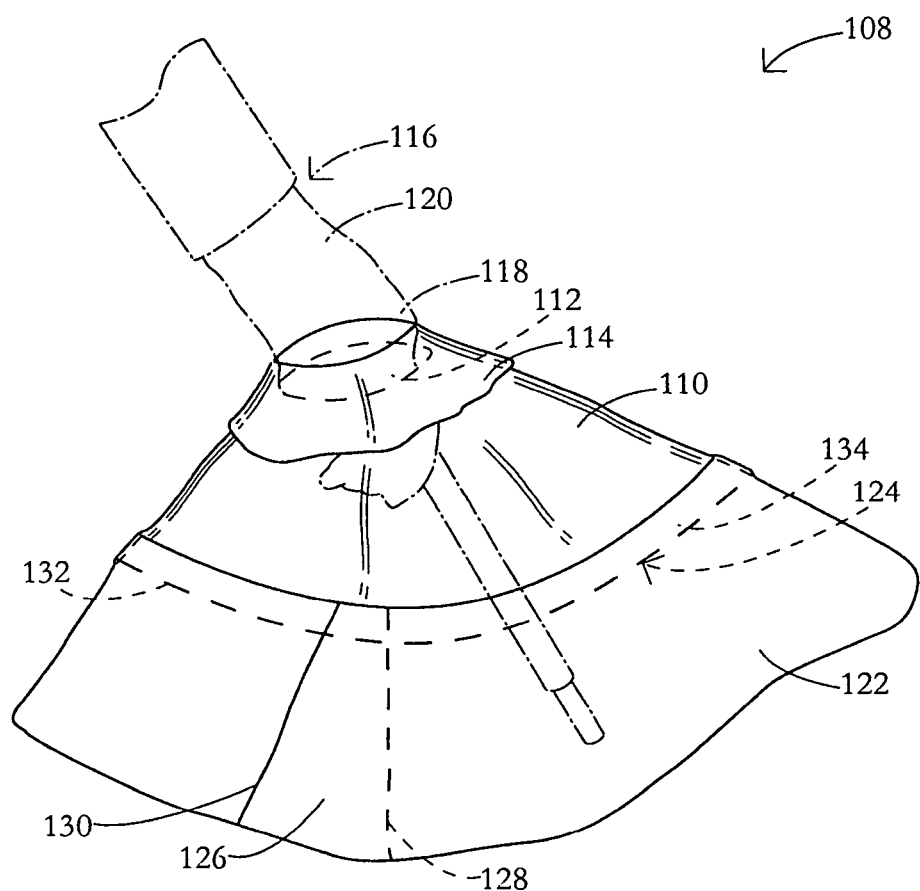
FIG. 9 is a schematic perspective view of yet a further surgical shield in accordance with the present invention.

As shown in FIG. 9, yet another surgical shield 108 includes a substantially frusto-conical shield support member 110 made of substantially rigid or at least semi-rigid transparent polymeric sheet or web material and eccentrically formed with an aperture 112. Aperture 112 is disposed more proximately to a rear edge section 132 of shield support member 110 than to a front edge section 134 thereby facilitating visual inspection of a surgical site through shield support member 110. A resilient coupling cuff 114 surrounds aperture 112 for sealingly engaging an appendage 116, particularly a hand 118 or a wrist 120, of a user. Cuff 114 may be made of polymeric foam material or take the form of an annular balloon that is inflatable about the user's appendage.

Shield 108 (FIG. 9) further includes a sheet or panel 122 of flexible transparent material that is attached to shield support member 110 along a peripheral edge 124 thereof to form a skirt. Sheet or panel 122 overlaps itself in a region 126 bounded by leading and trailing edges 128 and 130 of the sheet. Sheet or skirt 122 is exemplarily attached to shield support member 110 by adhesive or by thermal or ultrasonic welding.

Although the invention has been described in terms of particular embodiments and applications, one of ordinary skill in the art, in light of this teaching, can generate additional embodiments and modifications without departing from the spirit of or exceeding the scope of the claimed invention. It is to be understood that the structural and functional features of the various disclosed embodiments may be combined with one another to form other embodiments. For instance, the wrist cuff 114 of FIG. 9 may be alternatively provided in the embodiments of FIGS. 1-5, 7 and 8, while supporting extensions such as the fingers or ribs 86 and 96 of FIGS. 7 and 8 may be provided in the embodiments of FIGS. 1-5 and 9. Accordingly, it is to be understood that the drawings and descriptions herein are proffered by way of example to facilitate comprehension of the invention and should not be construed to limit the scope thereof.

What is claimed is:

1. A surgical method comprising:
   providing an ultrasonic surgical instrument and a shield comprising a shield support member in the form of an at least semi-rigid polymeric sheet or web member able to retain its shape under its own weight, said sheet or web member having an aperture and a perimeter and extending continuously in at least two spatial dimensions radially from said aperture to said perimeter, said shield further including at least one flexible sheet member attached to said shield support member so as to define an enclosure having one open side opposing said aperture, said at least one flexible sheet member having a free edge opposite said shield support member and defining said open side;
   inserting at least a distal end portion of said instrument through said aperture;
   releasably coupling said shield support member to a member taken from the group consisting of said instrument and an appendage of a user;
   manipulating said shield so as to place said open side of said enclosure against an exposed surface of a patient surrounding and spaced from a surgical site;
   thereafter operating said instrument to debride or ablate organic tissue at said surgical site; and
   during the operating of said instrument, manipulating said instrument and said shield so as to maintain said free edge of said at least one flexible sheet member in contact with the exposed surface of the patient around said surgical site, contact of said free edge of said at least one flexible sheet member with the exposed surface of the patient depending on the manipulating of said instrument and said shield.

2. The method defined in claim 1 wherein said at least one flexible sheet member forms a lateral wall of said enclosure, said shield support member forming an upper wall of said enclosure, said at least one flexible sheet member defining at least one access path into said enclosure through said lateral wall, further comprising inserting a distal end portion of an ancillary surgical instrument along said access path while said at least one flexible sheet member is in contact with the patient.

3. The method defined in claim 1 wherein the coupling of said shield to said instrument includes attaching said shield support member to a handle of said instrument.

4. The method defined in claim 1 wherein said instrument is an ultrasonic surgical device, the operating of said instrument including using said instrument to clean tissue at said surgical site.

5. The method defined in claim 1 wherein the manipulating of said instrument and said shield includes maintaining, during the operating of said instrument, said shield support member at such a distance from the patient that a vast majority of fluid droplets escaping said surgical site during operation of said instrument fail to reach said shield support member so that the surgical site remains effectively visible through the shield.

* * * * *